(12) United States Patent
Damadian

(10) Patent No.: US 11,317,860 B1
(45) Date of Patent: May 3, 2022

(54) METHOD AND SYSTEM FOR MONITORING EFFECTIVENESS OF A TREATMENT REGIMEN

(71) Applicant: Fonar Corporation, Melville, NY (US)

(72) Inventor: Raymond V. Damadian, Woodbury, NY (US)

(73) Assignee: Fonar Corporation, Melville, NY (US)

( * ) Notice: Subject to any disclaimer, the term of this patent is extended or adjusted under 35 U.S.C. 154(b) by 592 days.

(21) Appl. No.: 15/225,310

(22) Filed: Aug. 1, 2016

Related U.S. Application Data

(60) Provisional application No. 62/199,526, filed on Jul. 31, 2015.

(51) Int. Cl.
*A61B 5/00* (2006.01)
*A61B 5/055* (2006.01)

(52) U.S. Cl.
CPC ............ *A61B 5/4848* (2013.01); *A61B 5/055* (2013.01); *A61B 5/7271* (2013.01); *A61B 5/742* (2013.01); *A61B 2576/00* (2013.01)

(58) Field of Classification Search
CPC ..... A61B 5/4848; A61B 5/055; A61B 5/7271; A61B 5/742; A61B 2576/00
USPC ......................................................... 600/410
See application file for complete search history.

(56) References Cited

U.S. PATENT DOCUMENTS

| | | | |
|---|---|---|---|
| 6,414,490 B1 | 7/2002 | Damadian et al. | |
| 6,677,753 B1 | 1/2004 | Danby et al. | |
| 8,036,730 B1 * | 10/2011 | Damadian | A61B 5/0555 324/307 |
| 8,834,387 B2 | 9/2014 | Platt | |
| 2005/0054910 A1 * | 3/2005 | Tremblay | A61B 5/055 600/411 |
| 2006/0224539 A1 * | 10/2006 | Zhang | G06K 9/623 706/20 |
| 2007/0238954 A1 * | 10/2007 | White | A61B 8/481 600/407 |
| 2010/0284927 A1 * | 11/2010 | Lu | A61K 49/085 424/9.2 |
| 2011/0311026 A1 * | 12/2011 | Lalena | A61B 6/545 378/98.5 |

(Continued)

OTHER PUBLICATIONS

Damadian, Tumor Detection by Nuclear Magnetic Resonance, Science, vol. 171, pp. 1151-1153, Mar. 1971.

*Primary Examiner* — Amelie R Davis
*Assistant Examiner* — John Denny Li
(74) *Attorney, Agent, or Firm* — Lerner, David, Littenberg, Krumholz & Mentlik, LLP

(57) ABSTRACT

A method and system for assessing the effectiveness of a treatment regimen. In a preferred embodiment, baseline magnetic resonance imaging signals of a diseased portion of a subject's anatomy are acquired and image slices associated with diseased tissue or a selected region of interest are identified. The identified image slices are then stored and used in acquiring subsequent magnetic resonance imaging signals. The baseline and subsequently acquired magnetic resonance imaging signals are then processed to determine changes in location, size or other factors that provide an indication of whether treatment is effective. In another aspect, baseline and subsequent magnetic resonance parameters are also acquired and compared as part of determining the effective of treatment.

14 Claims, 5 Drawing Sheets

(56) References Cited

U.S. PATENT DOCUMENTS

| | | | | |
|---|---|---|---|---|
| 2012/0082352 A1* | 4/2012 | Hundley | ............... | A61B 5/0044 |
| | | | | 382/128 |
| 2012/0134552 A1* | 5/2012 | Boettger | .................. | G06T 7/12 |
| | | | | 382/128 |
| 2013/0131492 A1* | 5/2013 | Saranathan | ............ | A61B 5/055 |
| | | | | 600/410 |
| 2014/0055135 A1* | 2/2014 | Nielsen | .................. | G01R 33/58 |
| | | | | 324/309 |
| 2016/0213947 A1* | 7/2016 | Han | ..................... | A61N 5/1037 |
| 2018/0210053 A1* | 7/2018 | Piron | ..................... | A61B 5/035 |

\* cited by examiner

METHOD AND SYSTEM FOR MONITORING EFFECTIVENESS OF A TREATMENT REGIMEN

CROSS-REFERENCE TO RELATED APPLICATIONS

The present application claims the benefit of the filing date of U.S. Provisional Patent Application No. 62/199,526 filed Jul. 31, 2015, the disclosure of which is hereby incorporated herein by reference.

TECHNICAL FIELD

This disclosure relates to monitoring the effect of a disease treatment regimen in order to optimize the effectiveness of the treatment regimen utilized and in order to customize the treatment to particular physiology and disease condition of a subject.

BACKGROUND

Standard or typical treatment regimens are prescribed by physicians depending upon the particular disease or condition diagnosed in a patient. This is often done without regard for the physiology of the individual patient. In addition, depending upon the complexity or seriousness of a patient's medical condition, the effectiveness of a given treatment may not be closely monitored in time in order to assess its effectiveness quickly and not fruitlessly expend a critical period of the patient's survival time on an ineffective treatment regimen.

For example, before a follow-up assessment of the effectiveness of a treatment is made, a patient may be prescribed a cancer medication with the expectation that it may not manifest its expected result for an extended period of time. If, during the follow-up examination, the prescribed treatment is found to be ineffective, the period lost in the ineffective treatment trial period has been lost from the patient's ultimate survival period. Moreover, while the prescribed cancer medication may not work in the present example, it may prove effective for another individual whose physiology is different and/or whose cancer chemistry is different. This possible scenario underscores the need for early and frequent direct monitoring of the response of the lesion itself to the treatment regimen being employed so that treatment can be directly customized to the patient and customized specifically to the treatment response of the lesion itself.

The present disclosure provides method and systems that enable improved assessment of treatment of diseases or conditions of human subjects.

SUMMARY

In one aspect, the present invention includes methods that allow for more rapidly assessing lesion treatment effectiveness by direct image monitoring of the patient's lesion as he/she undergoes treatment to directly visualize the response (or lack thereof) of the patient to the treatment regimen being utilized. In instances such treatment is not deemed effective, it would enable modification of the treatment regimen (dosage changes or new treatment agents) to be customized for the patient until the desired lesion abatement is visually achieved, a prospect that the direct visualization of the lesion and its dimensions an chemistry (e.g., T1 and T2 measurements) by MRI has made possible. This is achieved through the use of the quantitative capabilities of tissue Magnetic Resonance, in addition to its well-known imaging capabilities (MRI), and the implementation of alternative treatment options in instances where a given treatment is proving ineffective or undesirable for any reason.

Magnetic Resonance is inherently capable of measuring the chemical/physical properties of the sample. This may be accomplished by, for example, measurement of the T1 and T2 relaxation times of a particular tissue in the body. T1 and T2 are quantitative measurements which have been demonstrated to correlate directly with the health and presence of disease in a tissue. Thus, in addition to providing the valuable image contrast (pixel contrast) in MRI imaging enabling image visualization of the patient's tissue pathologies, T1 and T2 are also separate quantities that can be directly quantified and which provide value in the detection (and diagnosis) of disease (see, e.g., Damadian, R., "Tumor Detection by Nuclear Magnetic Resonance," *Science*, 171: 1151-1153, 1971).

Another quantitative measurement available for the magnetic resonance diagnosis and characterization of disease is MR spectra. MR spectra are characterized by signal peaks which are shifted in frequency from each other thereby creating the spectra. Spectra represent the chemical signature of a particular nuclear species for a given tissue under investigation. The value of spectra is that the chemical signature has been shown to change with the state or severity of a disease, and provides another quantitative magnetic resonance measurement which can be employed to assess the effectiveness of a prescribed treatment regimen for an individual patient.

The quantitative measurements described above, as well as others, may be used in conjunction with traditional MR imaging to provide a more complete analysis of the patient's lesion(s) and its response (or lack of response) to the treatment regimen being utilized. Direct image monitoring and visualization of the responses of the patient's lesion to the therapeutic regimen being utilized would optimize the effectiveness of the treatment for optimum effectiveness.

The present disclosure includes methods and systems for more accurately assessing the morphology of tissues or other portions of human anatomy. In one aspect, a method for determining the effectiveness of a treatment regimen is disclosed. The method preferably comprises acquiring baseline magnetic resonance imaging signals of a portion of a subject's anatomy, identifying one or more image slices associated with a select portion of the subject's anatomy based on the acquired baseline magnetic resonance imaging signals, acquiring follow-up magnetic resonance imaging signals of the select portion of the subject's anatomy defined by the identified image slices, and comparing the baseline and follow-up magnetic resonance imaging signals of the select portion of the subject's anatomy to provide an indication of changes associated with the select portion of the subject's anatomy.

The method may further comprise acquiring baseline quantitative magnetic resonance parameters of the select portion of the subject's anatomy, acquiring follow-up quantitative magnetic resonance parameters of the select portion of the subject's anatomy and comparing the quantitative magnetic resonance parameters and follow-up quantitative magnetic resonance parameters to determine physiological changes in the select portion of the subject's anatomy.

The method may further comprise selecting the quantitative magnetic resonance parameters from the group consisting of T1 relaxation times, T2 relaxation times and magnetic resonance spectra. Further still, the physiological changes include physical and chemical changes of the select portion of the anatomy.

The method may also further comprise determining a baseline spatial location of the select portion of the subject's anatomy based on the acquired baseline magnetic resonance imaging signals.

In another aspect, comparing may comprise determining a follow-up spatial location of the select portion of the subject's anatomy based on the acquired follow-up magnetic resonance imaging signals and comparing the baseline and follow-up spatial location. In yet another aspect, comaring may comprise processing follow-up magnetic resonance image signals into follow-up image slices and comparing the identified and follow-up image slices to determine changes in location of the select portion of the subject's anatomy in the respective image slices.

Other aspects may include positioning scout scans for acquiring the follow-up magnetic resonance imaging signals at a location identical to the identified image slices as part of the comparison. In another further aspect, the indication of changes as baseline and follow-up magnetic resonance images may be displayed as overlayed on one another.

Another aspect may include a system. The system may comprise a magnetic resonance imaging apparatus; a memory storing instructions; a processor programmed using the instructions and configured to: receive baseline magnetic resonance imaging signals of a portion of a subject's anatomy acquired by the magnetic resonance imaging apparatus; identify one or more image slices associated with a select portion of the subject's anatomy based on the acquired baseline magnetic resonance imaging signals; receive follow-up magnetic resonance imaging signals of the select portion of the subject's anatomy defined by the identified image slices and acquired by the magnetic resonance imaging apparatus; and compare the baseline and follow-up magnetic resonance imaging signals of the select portion of the subject's anatomy to provide an indication of changes associated with the select portion of the subject's anatomy. The system may be configured and programmed in accordance with any of the foregoing or forthcoming aspects disclosed herein.

DETAILED DESCRIPTION

Figure 1:
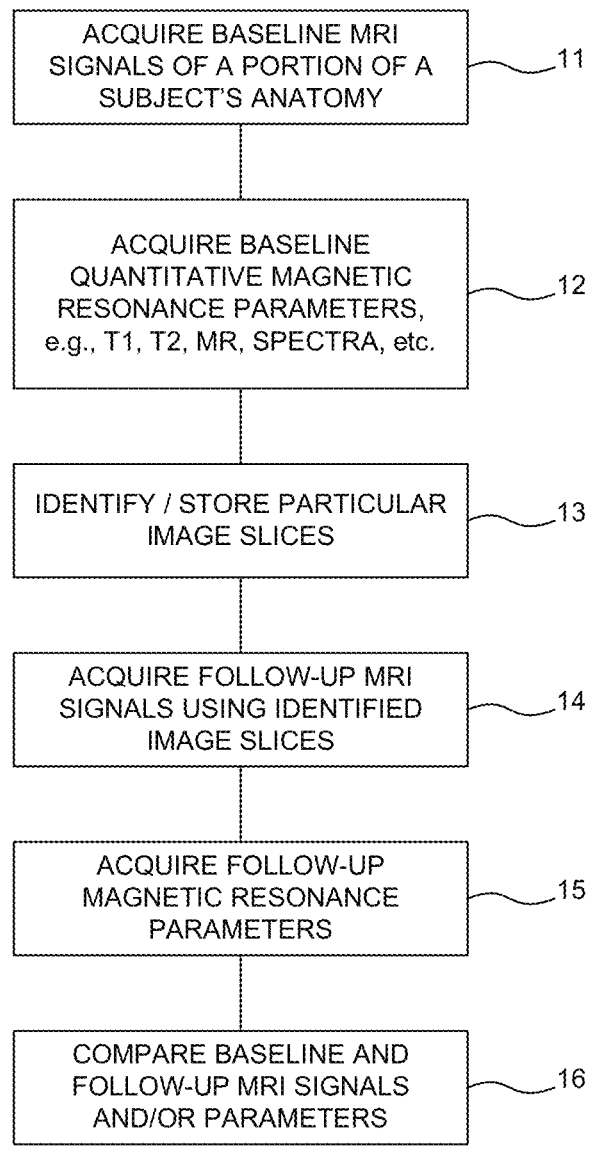
FIG. 1 depicts a flow diagram of an algorithm in accordance with an aspect of the disclosure.

In accordance with an aspect of the present invention, an individual may be diagnosed with some form of cancer based on the presence of a lesion discovered and visualized by an MRI examination as well as other corroborating medical testing and information. At this time, the spatial location of the lesion will be identified and some baseline quantitative magnetic resonance measurements of the lesion, such as T1, T2, MR spectra, or others will be made. Once a treatment regimen is prescribed and initiated, the progress and effectiveness of the treatment will be measured and monitored quantitatively by using, for example, the T1 and T2 relaxation times, the MR spectra, as well as MRI visual monitoring of the lesions physical dimensions, as frequently as desired, perhaps even weekly. Once the lesion has been physically located (i.e., the specific image slice on which the lesion is located) follow-up imaging protocols can be limited to acquiring only the lesion containing image slice, which would result in a marked reduction in the MRI scan time (and cost) of the monitoring procedure thereby facilitating its financial practicality (e.g., the single monitoring scan could be reduced to $75 from the $600 cost of the conventional multi-slice scan). The purpose of this monitoring is to determine as early as possible whether or not a prescribed treatment is being effective. Changes in a lesion which are identifiable in an MR image are preceded by changes in the chemical/physical nature of the lesion before such changes are actually manifest in the anatomy visualized by the MR image. Furthermore, the quantitative MR measurements proposed herein provide a valuable medical trail revealing either evidence of the hoped-for improvement in a patient's disease, or alternatively, evidence of the ineffectiveness of the treatment early on. In the case of the latter, there will be a need to either change the dosage of the prescribed medication, or customize a different treatment for the patient.

Another aspect of the present invention is the desire to make frequent and rapid quantitative MR measurements independent of traditional complete MR imaging studies. Frequent quantitative measurements of the tissue chemistry of a lesion takes advantage of the unique safety aspects of Magnetic Resonance not available with other imaging modalities. This aspect of the present invention is also necessary from the standpoint of the cost containment of medical procedures, and in order to provide such services to as many patients as possible. Once a lesion is identified in an initial diagnostic study, the location of the lesion is known. To conduct follow-up MR quantitative measurements frequently and rapidly then requires only a follow-up scan, in line with what was conducted in the original diagnostic MRI study where the lesion was originally discovered. Positioning the follow-up slices with the scout scan to certify that the anatomic positioning of the follow-up monitoring image slices are identical to the original multi-slice scan, and a process to bring both scans into direct image registration to enable an accurate assessment of the lesion's response to the treatment will be conducted. Positional offsets necessary for the registration of the images to occur will then be factored into any follow-up imaging procedure at that time. After the scout registration procedure is complete, the follow-up imaging procedure to locate the lesion may consist of only one, or the few images necessary to locate the extent of the lesion. The quantitative MR measurements as described herein will then be conducted, and assessments made as to the effectiveness of the treatment protocol, based upon comparison of the current values acquired during treatment with the quantitative MR measurements taken at an earlier time period prior to treatment.

Figure 2:
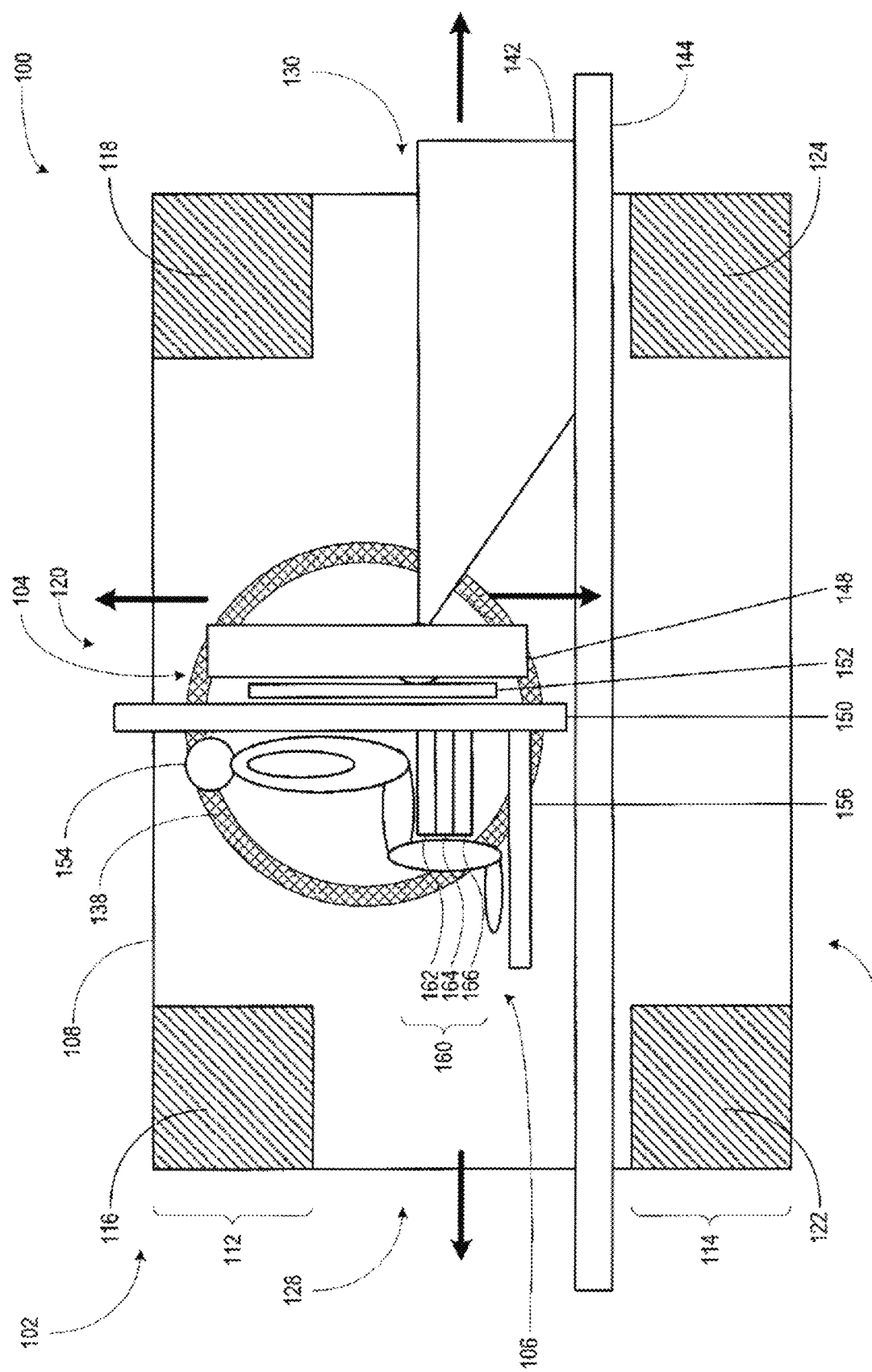
FIG. 2 depicts a magnetic resonance imaging apparatus that may be used in accordance with an aspect of the present invention.

FIG. 1 shows a flow diagram of a method 10 in accordance with an aspect of the present invention. The method begins with the acquisition of baseline magnetic resonance imaging ("MRI") signals of a portion of a subject's anatomy, block 11, which is of interest and desired to be imaged. The images may be acquired by a magnetic resonance imaging apparatus such as depicted in FIG. 2, which is discussed in further detail below. The type of magnetic resonance imaging apparatus is not limited, however, to that shown in FIG. 2. More conventional MRI apparatuses that include a tubular bore into which a recumbent patient is placed and image may also be used in accordance with the aspects of the present invention. The portion of the subject's anatomy may include any organ or other portion of the anatomy that is undergoing some form of medical treatment. In the preferred embodiment, as discussed above, the portion of the anatomy includes diseased tissue such as cancerous lesions, which are typically distinguishable from healthy tissue via MRI. Image acquisition may include first acquiring scout scans associated with a desired portion of the subject's anatomy and thereafter acquiring higher resolution multi-slices scans of that portion of the anatomy. In addition, as the acquired MRI signals contain positional information of the portion of the imaged anatomy, those signal can be further processed by a computing device, such as that discussed below, to derive information that defines the location of the imaged anatomy.

As shown at block 12, the method also includes acquiring baseline quantitative magnetic resonance imaging parameters associated with the portions of the subject's anatomy that has been imaged. Those parameters may include T1, T2 or MR spectra, but may also include other magnetic resonance parameters that provide a physiological marker, e.g., bio-chemical, mechanical or physical functions, of the portion of the subject's anatomy that was imaged. Such measurements may change over the course of treatment by different amounts and/or at different rates relative to each other. For example, measurements of T1 and T2 may change prior to visible changes of a lesion which are observed on an image. Following the various lesion characteristics over time may result in relatively independent indications of the effectiveness of a particular treatment regimen. These measurements may include the entire organ that was imaged or just diseased portion of the organ.

At block 13, the particular image slices associated with the diseased tissue or a specific region of the portion of the anatomy that was scanned are then identified and stored. Storage may occur at either the computing device used to operate the MRI apparatus or at a server or other computing device set aside for processing and storing MRI images. Identifying a subset of the multi-slice image previously acquired allows for pinpointing a selected region or area within the previously imaged portion of the anatomy. This advantageously allows for a reduction in time and costs, as discussed above for future MRI scans of the selected area that contains the diseased tissue of interest.

Next, follow-up MRI signals are acquired, block 14. These follow-up MRI signals are acquired using the image slices that were identified and stored at block 13. As discussed above, this allows for acquisition MRI signals or images that are focused on the selected area or region that contains diseased tissue. Follow-up imaging will typically take place at a later time depending on the treatment regimen or stage of disease. Typically, it will be determined by the amount of time typically required for a treatment regimen to have effect. At block 15, follow-up magnetic resonance parameters of the type acquired in block 120 are again acquired.

With the above signals and parameters acquired, the method then proceeds to block 16, which involves comparing the previously acquired baseline and follow-up MRI signals and/or magnetic resonance parameters. The acquired magnetic resonance imaging signals may be processed into images and displayed in a manner that shows difference in the location and size of the selected areas or regions of interest. Alternatively, the magnetic resonance image signals may be processed so as to compute actual changes in location and size, which is provided as an indication on display. The indication may for example include the direction and amount change in position or the percentage increase or decrease in volume of the size of the selected areas or regions of interest.

With regard to block 16, aspects of the invention include image registration, multi-planar tracking of lesion morphology and measurements of lesion characteristics. A key characteristic in tracking lesion morphology and measuring lesion characteristics is image registration. As one skilled in the art may appreciate, as a select portion of human anatomy is treated, e.g., a cancerous lesion, the anatomy reacts to treatment by changing its morphology. Therefore, comparison of the baseline and follow-up images to determine changes presents many challenges. For example, the shape of the anatomy may change in three dimensions and may even appear as if its changed location. Therefore, registration of the follow-up image(s) is important to help insure that measurements of lesion characteristics such as lesion size, T1, T2 and MR spectra are made in the same anatomical region of interest that was initially identified, and where any of the initial scan measurements were made. Image registration may be accomplished in numerous ways. For example, in a case where the region of interest is identified in an axial image, an orthogonal image such as a sagittal image may be used to determine a location for the follow-up axial scan. This may be accomplished by positioning the follow-up scan acquisition at a particular vertebral location of the spine—for example a particular cervical, thoracic, or lumbar vertebra—where the initial scan was made. This procedure would help insure that proper image registration occurs. In addition, once the follow-up image is acquired it may be normalized with respect to the baseline image by tracing the contours of the follow-up image and then finding contour matches on the baseline image. Such contour matching may begin at a location where the lesion is actually attached to other anatomy, e.g., the above referenced portion of the anatomy in the scan, and then fan out three dimensional through the magnetic resonace image formed using the captured magnetic resonance imaging signals.

In more detail, tumors or lesions may extend in three dimensions, and therefore, it may be desirable to follow changes in lesion size in more than one image plane. This recognizes the possibility that the morphology of a lesion may change to a different extent in different directions. That is, a lesion may shrink or expand in size in one direction but not necessarily in the same way in other directions. Monitoring lesion size over time in more than one direction may, in certain circumstances, give a more representative assessment of the effectiveness of a particular treatment regimen.

Turning now to FIG. 2, there is shown an FIG. 1 illustrates an exemplary MRI apparatus 100 for imaging a subject according to aspects of the disclosure. In one embodiment, the MRI apparatus 100 includes a magnet having a ferromagnetic frame 102, a magnetic flux generator 104, and a patient handling system 106. The ferromagnetic frame 102 includes a first side wall 108 and a second side wall. The side walls extend vertically. As FIG. 1 is a sectional view of the MRI apparatus 100, FIG. 1 does not show the second side wall or any of its associated structures for clarity. The second side wall would include all the components necessary to complete the path for a magnetic circuit or loop, e.g., a corresponding pole or an electromagnetic coil assembly to that shown in FIG. 1 with reference numeral 138, etc.

The ferromagnetic frame 102 may also include a top flux return structure 112 and a bottom flux return structure 114.

The top flux return structure 112 may include two columnar structures 116 and 118. Between these two columnar structures, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 defines a front patient opening 128 on one side of the frame and a similar back patient opening 130 on the opposite side of the frame.

The ferromagnetic frame further includes a first magnetic pole and a second magnetic pole. The first magnetic pole extends from the first side wall 108 towards the second side wall and the second magnetic pole extends from the second side wall towards the first side wall 108. The magnetic poles are generally cylindrical and are coaxial with one another on a common horizontal polar axis. Between the magnetic poles is a gap accessed by the front patient opening 128, the back patient opening 130, the top opening 120 or the bottom opening 126.

The magnetic flux generator 104 includes a first electromagnetic coil assembly 138 magnetically coupled to ferromagnetic frame 102, proximate to side 108, and parallel to side 108. The magnetic flux generator 104 also includes a second electromagnet coil assembly (not shown) magnetically coupled to ferromagnetic frame 102, proximate to the second side wall, and parallel to the second side wall. As previously noted, these electromagnetic coil assemblies 138 and 140 may be either resistive or superconductive. Alternatively, the magnetic flux generator 104 may be a permanent magnet. The magnetic flux generator 104 may be configured to emit a magnetic field $B_0$ along one or more axes. The magnetic flux generator 104 may also include one or more gradient coils (not shown) for inducing a gradient in the $B_0$ magnetic field. The $B_0$ magnetic field generally extends horizontally parallel to support surface of the apparatus from one side wall to the other. The support surface will generally be the floor of a building or facility housing the apparatus 100.

The apparatus 100 may further include a patient support assembly 106 including a chair or seat assembly 160 on which a patient is capable of sitting. The patient handling system 106 is capable of three degrees of motion. The patient handling system further supports positioning of a patient in the Trendelburg and reverse-Trendleburg orientations. Generally, the degrees of motion allow for positioning of the patient in a variety of orientations or positions. The patient handling system 106 may include a carriage 142 mounted on rails 144. The carriage 142 may move linearly back and forth along the rails 144. The rails 144 typically do not block the bottom open space 126.

A generally horizontal pivot axis is mounted on carriage 142. An elevator frame 148 is mounted to the pivot axis. The carriage 142 is operable to rotate the elevator frame 148 about the pivot axis. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement. Specifically, the patient handling system 106 can move a patient 154 in two linear directions and also rotate patient 154 around an axis. The solid black arrows of FIG. 1 show various axes of movement possible with the patient handling system 106. Note that often the rails 108 are mounted such that portions of patient 154 may be positioned below the rails through bottom open space 126.

The apparatus 100 may be configured such that the seat assembly 160 is not present. In that configuration, the patient would then be allowed to stand on the support 156. Allowing the patient to sit or stand, or more generally to remain in an upright position during image, has many advantages. For example, blood and CSF flow will be different in the upright position than in a recumbent position and may reveal. In addition, upright imaging of CSF flow may reveal abnormal conditions.

In making MRI measurements, the patient is fitted with an antenna coil that receives magnetic resonance signals from the region of interest of the subject's anatomy being imaged. Such antennas are placed at on or proximate the patient and may include a variety of geometries that maximize the signal strength and signal-to-noise (S/N) ratios of the magnetic resonance signals emitted by the anatomy of interest. Such antennas may include head coils to capture image signals associated with the head, neck or upper spine. Other antennas may include coils that are place proximate the back or spinal column. As another example, the patient support assembly 106 may include a seat assembly 160 may include a quadrature coil arrangement. In particular, the seat assembly 160 may include a seat or sitting surface 166, an enclosure 162 containing a contoured quadrature coil, and a cushion 164. The enclosure 162, which is shown as being adjacent to patient 154, may then the contoured quadrature coil having a normal vector transverse to the horizontal pole axis of the magnetic poles of the MRI apparatus 100, and thus transverse to the magnetic field vector parallel to the horizontal pole axis.

Additional views and disclosure of an MRI apparatus of the type discussed above may be found by reference to U.S. Pat. No. 6,677,753, the disclosure of which is incorporated herein by reference. Alternative embodiments of the MRI apparatus also include those discussed in U.S. Pat. No. 6,414,490, the disclosure of which is also incorporated by reference. In addition, the magnetic resonance image apparatus does not necessarily need to include ferromagnetic frames or poles. For example, an apparatus such as that disclosed in commonly assigned U.S. Pat. No. 8,384,387, the disclosure of which is incorporated by reference herein, may comprise the magnetic resonance imaging apparatus in accordance with the various aspects of the present invention.

As previously mentioned above, the MRI apparatus need not be limited to that shown in FIG. 2 but may include conventional less open bore type geometries.

Figure 3A:
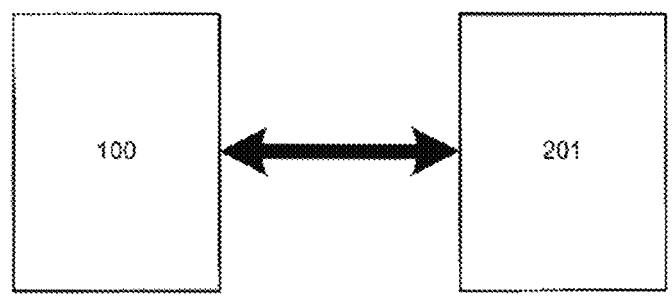
FIGS. 3A and 3B, respectively, depict embodiments of systems that may be used in accordance with an aspect of the present invention.

As discussed above, the magnetic resonance imaging signals and magnetic resonance parameters that acquired using the MRI apparatus 100 are processed by a computing device in performing the method discussed above and shown in FIG. 1. Generally, the computing device 201 and apparatus 100 may be arranged as part of a system 200 as shown in FIG. 3A. The computing device 201 is programmed using instructions that cause it to receive magnetic resonance imaging signals, as well as the magnetic resonance parameters, from the apparatus 100 and thereafter process those signals and parameters in accordance with further instructions.

Figure 3B:
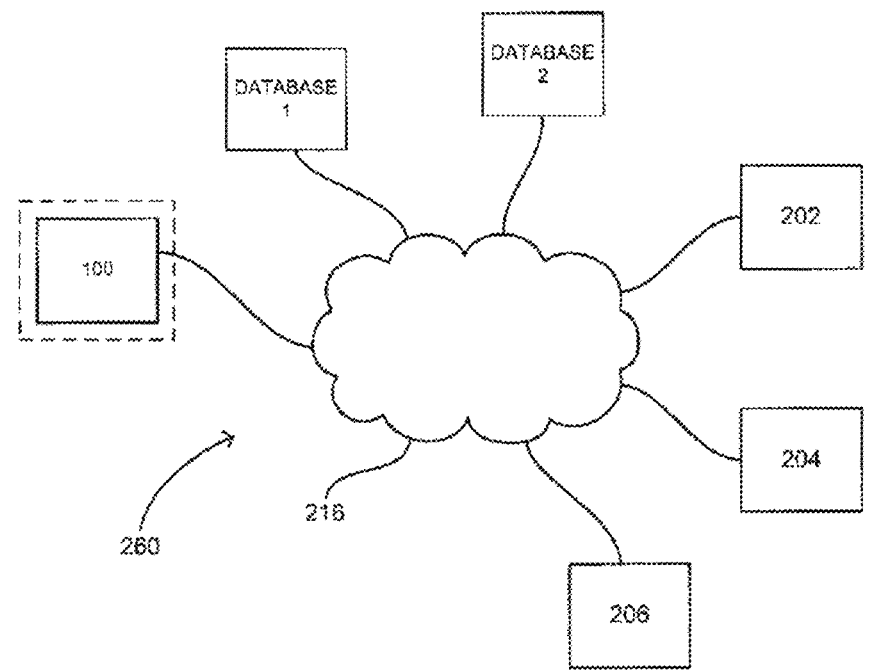

The system 200 may be part of a computer network as shown in FIG. 3B. The illustration of FIG. 3B presents a schematic diagram of a computer system depicting various computing devices that can be used alone or in a networked configuration in accordance with aspects of the invention. For example, this figure illustrates a computer network 260 having a plurality of computers 202, 204 and 206. The network 260 may include other types of devices such as mobile phones or PDAs. Various elements in the computer network 260 may be interconnected via a local or direct connection (such as shown in FIG. 3A) and/or may be coupled via a communications network 216 such as a local area network ("LAN"), a WiFi network, a wide area network ("WAN"), the Internet, etc. and which may be wired or wireless. The communications network 216 may include a plurality of nodes having routers, servers, wireless access points, etc.

Figure 3C:
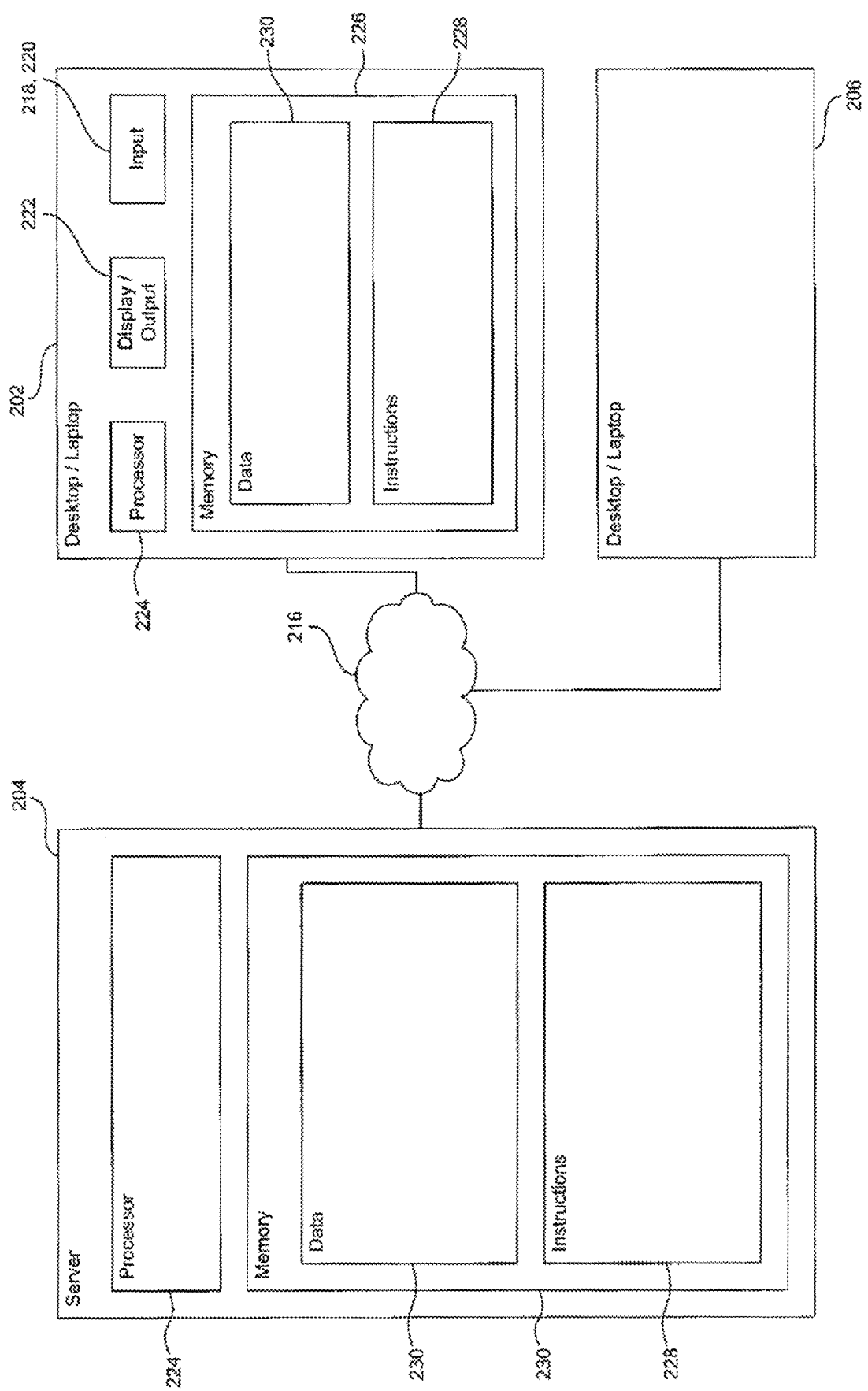
FIG. 3C depicts computing device connected via a network in accordance with an aspect of the present invention.

Each computing device can include, for example, one or more computers having user inputs such as a keyboard and mouse and/or various other types of input devices such as pen-inputs, joysticks, buttons, touch screens, etc., as well as a display, which could include, for instance, a CRT, LCD, plasma screen monitor, TV, projector, etc. Each computer 202, 204 and 206 may be a personal computer, server, etc. By way of example only, computer 202 may be a desktop computer, while computer 204 may be a server, and computer 206 may be a laptop. As shown in FIG. 3C each computer, such as computers 202 and 204, contains a processor 224, memory 226 and other components typically present in a computer.

With continued reference to FIG. 3C, memory 226 stores information accessible by processor 224, including instructions 228 that may be executed by the processor 224 and data 230 that may be retrieved, manipulated or stored by the processor. The memory may be of any type capable of storing information accessible by the processor, such as a hard-drive, ROM, RAM, CD-ROM, DVD, Blu-Ray disk, flash memories, write-capable or read-only memories. The processor 224 may comprise any number of well known processors, such as processors from Intel Corporation. Alternatively, the processor may be a dedicated controller for executing operations, such as an ASIC.

The instructions 228 may comprise any set of instructions to be executed directly (such as machine code) or indirectly (such as scripts) by the processor. In that regard, the terms "instructions," "steps" and "programs" may be used interchangeably herein. The instructions may be stored in any computer language or format, such as in object code or modules of source code. The functions, methods and routines of instructions in accordance with the present invention are explained in more detail below.

Data 230 may be retrieved, stored or modified by processor 224 in accordance with the instructions 228. The data may be stored as a collection of data. For instance, although the invention is not limited by any particular data structure, the data may be stored in computer registers, in a relational database as a table having a plurality of different fields and records, XML documents, or flat files. Map-type image data may be stored in flat files such as keyhole flat files ("KFF"). Content and advertising data may be stored in one or more relational databases.

The data may also be formatted in any computer readable format such as, but not limited to, binary values, ASCII etc. Similarly, the data may include images stored in a variety of formats such as vector-based images or bitmap images using lossless (e.g., BMP) or lossy (e.g., JPEG) encoding. Moreover, the data may include any information sufficient to identify the relevant information, such as descriptive text, proprietary codes, pointers, references to data stored in other memories (including other network locations) or information which is used by a function to calculate the relevant data.

Although the processor 224 and memory 226 are functionally illustrated in FIG. 3C as being within the same block, it will be understood that the processor and memory may actually comprise multiple processors and memories that may or may not be stored within the same physical housing or location. For example, some or all of the instructions and data may be stored on a removable recording medium such as a CD-ROM, DVD or Blu-Ray disk. Alternatively, such information may be stored within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 126 such as hard drives, data centers, server farms or the like.

In one aspect, the computing device 204 comprises a server. The other computing devices 202, 206 computer may be a general purpose computer, intended for use by a person, having all the components normally found in a personal computer such as a central processing unit ("CPU"), display, CD-ROM, DVD or Blu-Ray drive, hard-drive, mouse, keyboard, touch-sensitive screen, speakers, microphone, modem and/or router (telephone, cable or otherwise) and all of the components used for connecting these elements to one another.

The server and computers are capable of direct and indirect communication with other computers, such as over network 216. The network 216, including any intervening nodes, may comprise various configurations and protocols including the Internet, intranets, virtual private networks, wide area networks, local networks, private networks using communication protocols proprietary to one or more companies, Ethernet, WiFi, Bluetooth and HTTP.

Communication across the network, including any intervening nodes, may be facilitated by any device capable of transmitting data to and from other computers, such as modems (e.g., dial-up or cable), network interfaces and wireless interfaces. Server 204 may be an application server such as a web server.

Although certain advantages are obtained when information is transmitted or received as noted above, other aspects of the invention are not limited to any particular manner of transmission of information. For example, in some aspects, the information may be sent via a medium such as a disk, tape, CD-ROM, DVD, Blu-Ray disk or directly between two computer systems via a dial-up modem. In other aspects, the information may be transmitted in a non-electronic format and manually entered into the system.

The networked architecture 260 shown in FIG. 3B provides some flexibility in implementing the system. For example, the more complex processing may be done on the server 204, while the computer 202 may be used to control the actual acquisition of magnetic resonance signals from the apparatus 100. For example, the server may, in accordance with the discussions above, process the magnetic resonance signals it receives from computer 202 to do the comparison in block 160 of FIG. 1 and display the results on of the other computing devices in a web-server environment.

Databases 1 and 2 are preferably used to store patient data, such as images resulting from MRI scans. The databases may also be used to store other data, as well as the computer code or instructions that the server and/or computers use to perform the measurements and methods disclosed herein.

Figure 4:
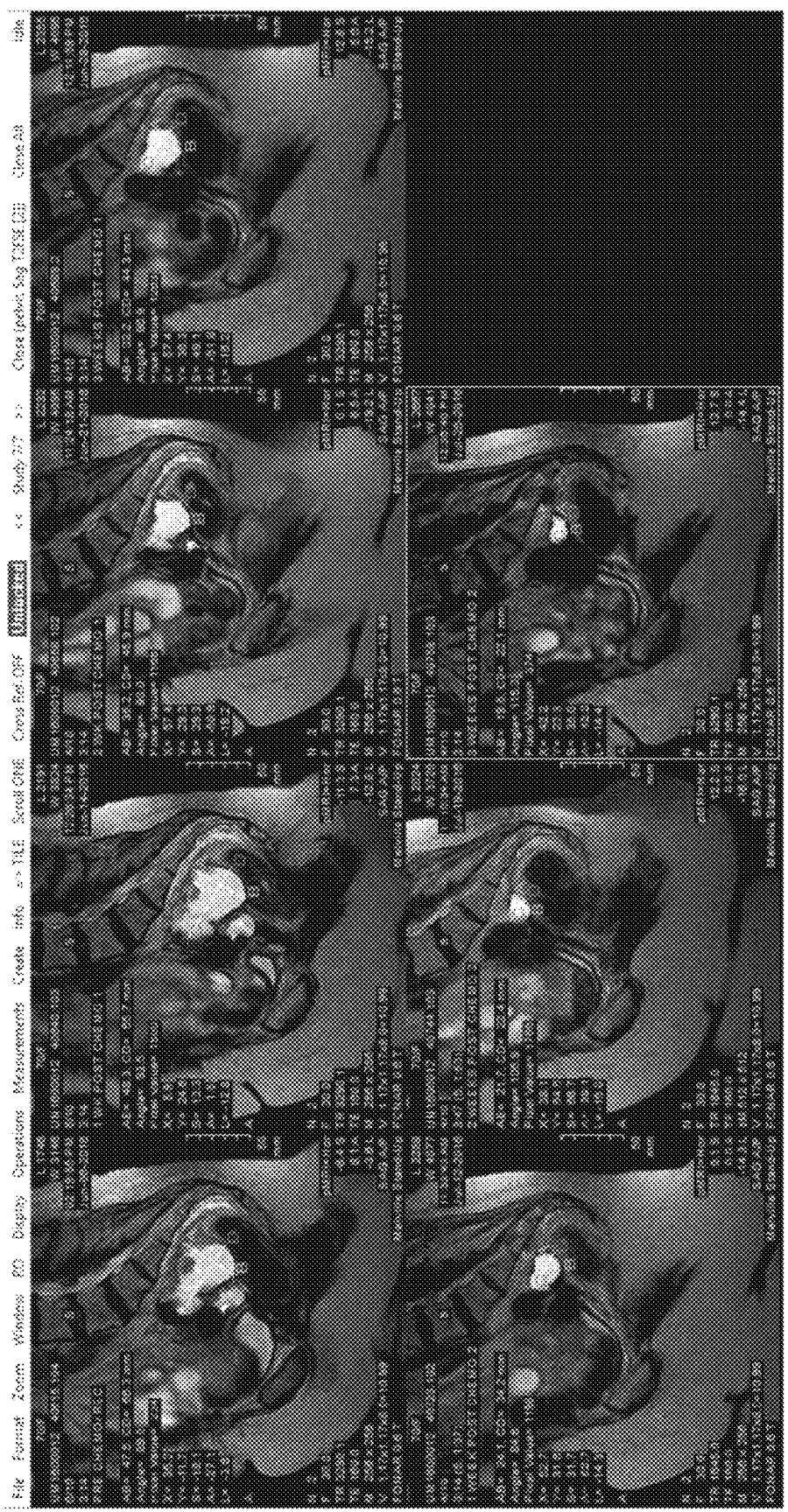
FIG. 4 are images captured in accordance with an aspect of the present invention.

FIG. 4 depicts images captured, processed and displayed using the system depicted in FIGS. 3A and 3B. The images show the change in morphology in a lesion whose size is traced using the cross-sectional lines A, B, C and D. As the drawings show, the measurements AB and CD were reduced over the time sequence indicating a marked reduction in size of the lesion. Thus, (For example, prior to beginning the treatment regimen, the lesion dimensions were AB=47.5 mm and CD=66.3 mm as can be seen in FIG. 4, the size of the lesion progressively diminished over the time course of the treatment. Indeed, in the final image taken at the end of the treatment period shown, the lesion dimensions were AB=19.5 mm and CD=22.1 mm.) As indicated in the pictures, the lesion changed its morphology which required processing as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for determining an effectiveness of a treatment regimen for a subject, comprising:
   during a first imaging session of the subject, acquiring baseline magnetic resonance imaging signals from a plurality of baseline image slices and baseline quantitative magnetic resonance parameters of the select portion of the subject's anatomy, wherein the baseline quantitative magnetic resonance parameters comprise baseline magnetic resonance spectra;
   identifying a select portion of the subject's anatomy to receive the treatment regimen;
   determining which one or more of the plurality of baseline image slices the select portion of the subject's anatomy is present in based on the acquired baseline magnetic resonance imaging signals;
   during a second imaging session of the subject:
      acquiring a scout magnetic resonance image of the subject, wherein the plurality of baseline image slices are orthogonal to a plane of the scout magnetic resonance image;
      aligning a plurality of follow-up image slices of the scout magnetic resonance image with the plurality of baseline image slices conducting image by registration of the scout magnetic resonance image;
      acquiring follow-up magnetic resonance imaging signals from only follow-up image slices aligned with those baseline image slices that the select portion of the subject's anatomy was determined to be present in during acquisition of the baseline magnetic resonance imaging signals and follow-up quantitative magnetic resonance parameters of the select portion of the subject's anatomy, wherein the follow-up quantitative magnetic resonance parameters comprise follow-up magnetic resonance spectra;
   comparing the baseline and follow-up magnetic resonance spectra of the acquired baseline and acquired follow-up magnetic resonance parameters of the select portion of the subject's anatomy;
   determining a change to the select portion of the subject's anatomy based on the comparison of the baseline and follow-up resonance spectra; and
   determining, based on the determined change to the select portion of the subject's anatomy, the effectiveness of the treatment regimen.

2. The method of claim 1, wherein the quantitative magnetic resonance parameters further comprise one or more of T1 relaxation times and T2 relaxation times.

3. The method of claim 1, further comprising determining chemical changes of the select portion of the anatomy based on a comparison of the acquired baseline and acquired follow-up magnetic resonance imaging signals of the select portion of the subject's anatomy, wherein the effectiveness of the treatment regimen is further determined based on the chemical changes.

4. The method of claim 1, wherein registration of the scout magnetic resonance image is based on a comparison between anatomic positioning of the subject in a baseline scout magnetic resonance image acquired during the first imaging session and the scout magnetic resonance image acquired during the second imaging session.

5. The method of claim 4, wherein the comparison between anatomic positioning of the subject in the baseline scout magnetic resonance image acquired during the first imaging session and the scout magnetic resonance image acquired during the second imaging session comprises determining an offset.

6. The method of claim 4, wherein the comparison between anatomic positioning of the subject in the baseline scout magnetic resonance image acquired during the first imaging session and the scout magnetic resonance image acquired during the second imaging session comprises:
   normalizing the scout magnetic resonance image with the baseline scout magnetic resonance image; and
   contour matching the scout magnetic resonance image with the baseline scout magnetic resonance image,
   wherein the normalized and contour matched follow-up image slices are aligned with the baseline image slices.

7. The method of claim 6, wherein contour matching the scout magnetic resonance image with the baseline scout magnetic resonance image comprises:
   identifying a location at which a lesion in the select portion of the subject's anatomy is attached to other anatomy;
   contour matching at the identified location.

8. The method of claim 7, wherein the contour matching is performed three-dimensionally through the scout magnetic resonance image based on the captured magnetic resonance imaging signals.

9. The method of claim 1, further comprising, during the first imaging session, acquiring a baseline scout magnetic resonance image of a subject, wherein the plurality of baseline image slices are orthogonal to a plane of the baseline scout magnetic resonance image, and
   wherein the follow-up magnetic resonance imaging signals are acquired based on a positioning of the image slices which the select portion of the subject's anatomy was determined to be present in the follow-up scout magnetic resonance image.

10. The method of claim 1, further comprising displaying the indication of changes as the acquired baseline and acquired follow-up magnetic resonance images overlayed on one another.

11. The method of claim 1, further comprising determining a change in size or shape of the select portion of the subject's anatomy based on comparing the acquired baseline and acquired follow-up magnetic resonance parameters of the select portion of the subject's anatomy, wherein the effectiveness of the treatment regimen is determined based on the change in size or shape.

12. The method of claim 11, wherein the baseline magnetic resonance imaging signals and the follow-up magnetic resonance imaging signals are acquired during separate imaging sessions of the subject.

13. The method of claim 1, wherein the first and second imaging sessions are weekly imaging sessions.

14. The method of claim 1, wherein the change to the select portion of the subject's anatomy is determined based on a pixel contrast between the acquired baseline and acquired follow-up magnetic resonance imaging signals of the select portion of the subject's anatomy.

* * * * *